United States Patent [19]

Chiodo

[11] Patent Number: 4,802,645
[45] Date of Patent: Feb. 7, 1989

[54] SYRINGE HOLDER

[76] Inventor: Gary T. Chiodo, 7015 SE. 34th Ave., Portland, Oreg. 97202

[21] Appl. No.: 151,227

[22] Filed: Feb. 1, 1988

[51] Int. Cl.⁴ .............................................. A47F 5/00
[52] U.S. Cl. ................................ 248/309.1; 248/231.7
[58] Field of Search ...................... 248/309.1, 231.7; 211/60.1, 69, 13; 604/192, 193, 263; 206/364, 365, 285; 128/DIG. 6

[56] References Cited

U.S. PATENT DOCUMENTS

| | | | |
|---|---|---|---|
| 2,509,793 | 5/1950 | Yost | 248/314 X |
| 2,547,507 | 4/1951 | Sucksdorf | 248/316.1 X |
| 2,720,189 | 10/1955 | Newman | 211/60.1 X |
| 3,261,660 | 7/1966 | Wilkinson | 211/60.1 X |
| 3,642,123 | 2/1972 | Knox | 206/285 X |
| 4,425,120 | 1/1984 | Sampson et al. | 604/198 |
| 4,507,117 | 3/1985 | Vining et al. | 604/196 |
| 4,573,976 | 3/1986 | Sampson et al. | 604/196 |
| 4,592,744 | 6/1986 | Jagger et al. | 604/192 |
| 4,610,667 | 9/1986 | Pedicano | 604/263 X |
| 4,631,057 | 12/1986 | Mitchell | 604/198 |
| 4,643,722 | 2/1987 | Smith, Jr. | 604/192 |
| 4,666,435 | 5/1987 | Braginetz | 604/198 |
| 4,681,567 | 7/1987 | Masters et al. | 604/198 |
| 4,693,708 | 9/1987 | Wanderer | 604/198 |
| 4,735,617 | 4/1988 | Nelson | 604/192 |

Primary Examiner—J. Franklin Foss
Attorney, Agent, or Firm—Eugene D. Farley

[57] ABSTRACT

A syringe holder permitting one-handed recapping of the syringe needle and thereby avoiding possibility of injury from needlestick.

The holder comprises a support for the syringe body associated with a support for the needle cap. A clamp is provided for the needle cap support which releasably clamps the cap in place during use of the syringe. Accordingly the syringe needle may be withdrawn from the cap and recapped as many times as desired, using but a single hand. A sheath is associated with the assembly.

3 Claims, 1 Drawing Sheet

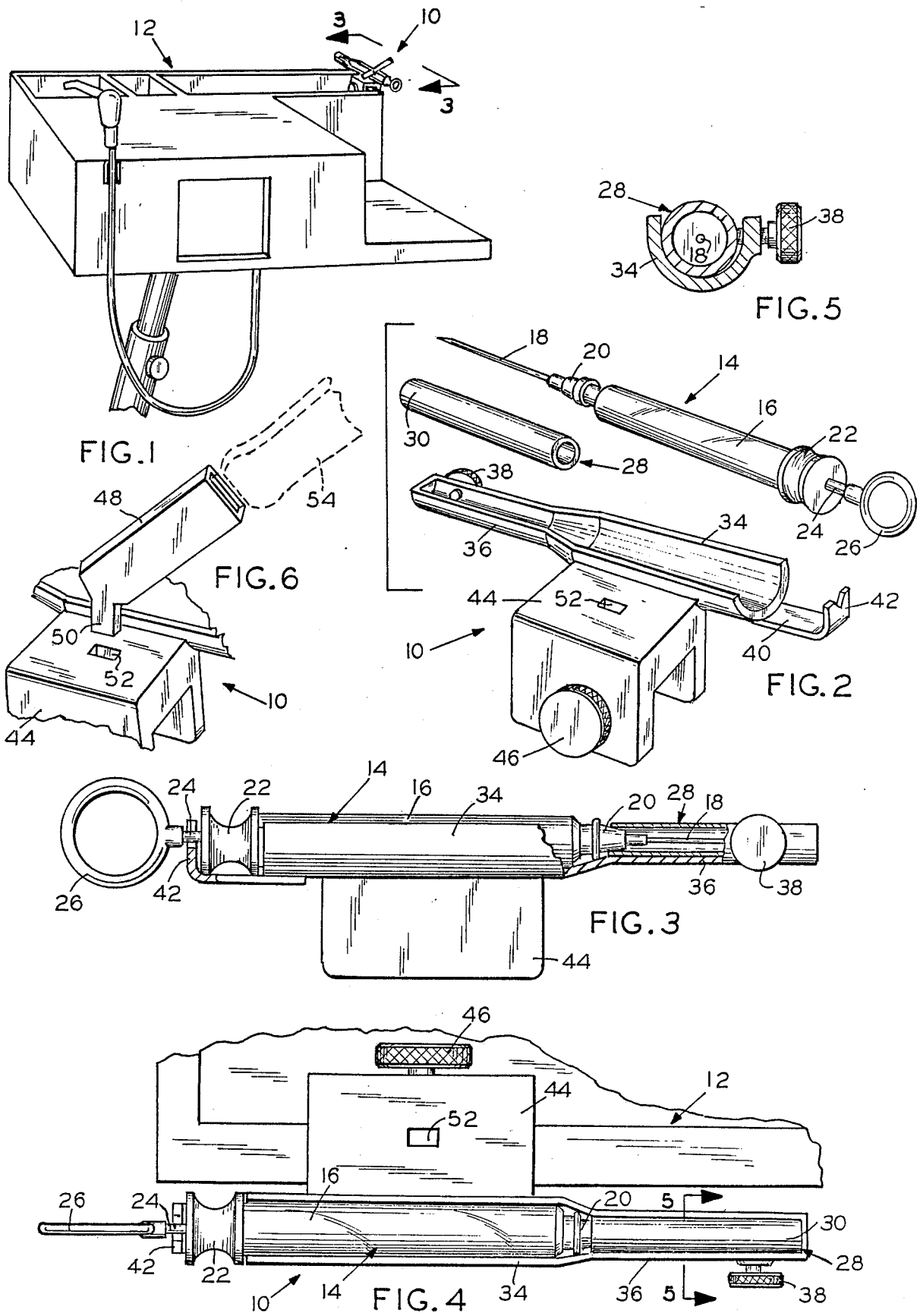

SYRINGE HOLDER

SYRINGE HOLDER

This invention pertains to syringe holders. It pertains particularly to holders provided with safety caps for preventing needlesticks.

BACKGROUND AND GENERAL STATEMENT OF THE INVENTION

"Needlestick" is the term applied to the inadvertant puncturing of the skin by the needle of a hypodermic syringe. Accidental needlesticks are of great concern, particularly when the needle previously has been used for injecting, or taking blood samples from, an infected patient. A subsequent inadvertent needlesticking episode may result in the transmission of deadly diseases such as hepatitis, herpes, tuberculosis, venereal diseases, and, of most recent concern: AIDS.

To date, almost all cases of aids transmission to health care workers who are not otherwise in a high risk group, have been caused by needlestick injury. Various expedients heretofore have been proposed for combating this problem.

Syringes have been equipped with retractable sheaths which cover the needle during periods of non-use. Clipping devices have been provided for clipping the needles after use. Syringes have been provided with retractable needles.

The most common practice, however, is to provide hypodermic needles with removable caps that protect the needles and help keep them sterile. The cap is replaceable to cover the used, contaminated needle and prevent accidental needlesticks. sticks.

In spite of this, accidental needlesticks are still of relatively common occurrence. Up to now, in order to recap the needle it has been necessary to hold the cap between the fingers of one hand (or, worse, between the teeth or lips) and, with a puncturing motion advance the needle into the cap. Such "two-handed" recapping leads to puncturing type accidents because of personnel stress, fatigue, time pressure, and related factors.

Even in situations where needle recapping is not practiced, the possibility of injurious contact with used and contaminated needles is not eliminated. There still remains the possibility of such contact with discarded, used needles which have accumulated on instrument trays, counter tops, in sinks, and in refuse containers.

The problem is particularly acute in the practice of dentistry. In such a practice, it is usual to administer the local anesthetic by means of a hypodermic syringe. The injections often are given serially, i.e. at intervals over a period of time. During serial administration it frequently is necessary to recharge the syringe with one or more additional anesthetic cartridges.

These operations require frequent handling of the syringe by the dentist and the dental assistant. If the usual two-handed recapping technique is used between each use episode, the opportunities for the occurrence of a needlestick type injury are multiplied correspondingly.

It is the general purpose of the present invention to prevent the occurrence of needlestick injuries of the type described above.

It is a further important object of the present invention to prevent the occurrence of needlestick injuries by providing a syringe holder which makes mandatory single-handed recapping of the hypodermic needle. Where but a single hand is employed, the possibility of puncturing the skin of the second hand or other body area during recapping obviously is eliminated.

It is a further important object of the present invention to provide an appliance of the class described which is simple in construction, easily mountable on a dental or other medical instrument cart, inexpensive, and adaptable for autoclaving.

Still a further object of the present invention is the provision of a syringe holder which may be associated to advantage with a scalpel holder having like advantages with the result that the hazard attending the use of both of these potentially hazardous implements is eliminated.

The foregoing and other objects of the present invention are achieved by the provision of a syringe holder which, in essence, comprises a base coupled with releasable attaching means for mounting it upon a structural element of a medical instrument cart or other structure. A syringe body support is mounted on the base. A cap support is mounted at one end of the body support, arranged substantially co-axially therewith, with the open end of the support facing inwardly.

Releasable cap securing means is positioned for releasably securing the cap in a position to receive the syringe needle when the syringe body is placed in the syringe body support, to secure the cap when the syringe is removed from the support and to release the cap when the syringe and cap are removed from the support together for disposal after each syringe use. During this sequence, the medical professional need only use one hand. The possibility of needlestick accordingly is eliminated.

Associated with the syringe holder there may be an accompanying scalpel holder functioning in analagous manner.

THE DRAWINGS

In the drawings:

FIG. 1 is a top perspective view of a medical instrument cart with the herein described syringe holder affixed thereto.

FIG. 2 is an exploded view in top perspective of a typical hypodermic syringe and the herein described holder therefor, the items being illustrated in their working relationship to each other.

FIG. 3 is a view in side elevation of the herein described syringe holder, partly in section, with a syringe mounted thereon, looking in the direction of the arrows of line 3—3 of FIG. 1.

FIG. 4 is a plan view of the holder, with the syringe in place therein.

FIG. 5 is a transverse sectional view taken along line 5—5 of FIG. 4.

FIG. 6 is a fragmentary perspective view of a scalpel holder associated with the clamp member component of the syringe holder.

DESCRIPTION OF A SPECIFIC EMBODIMENT OF THE INVENTION

In FIG. 1 the syringe holder 10 of my invention is illustrated mounted in a typical manner on dental cart 12.

A typical syringe which the holder is adapted to support is indicated generally at 14.

As illustrated particularly in FIG. 2, the syringe comprises a syringe body or barrel 16, a syringe needle 18, and a coupling 20 by means of which the needle may be releasably coupled to the body.

The syringe assembly further includes a finger grip 22, a plunger 24, and an operating loop or thumb hole 26 attached to the outer end of the plunger. The latter elements of the assembly are located at the end of barrel 16, opposite the end which mounts needle 18.

A typical cap, indicated generally at 28, is also illustrated in FIG. 2. It comprises a cylindrical body 30 closed at one end and open on the other.

The length of the cap is sufficient to accommodate the entire length of needle 18. The diameter of its open end is such as to provide a friction fit with coupling 20 when the cap is placed in position, sheathing the needle. It thus is readily removable and replaceable, as desired.

Again referring to FIG. 2, holder 10 comprises a syringe body support 34 which preferably is cradled-shaped and dimensioned to receive the body 16 of the syringe. It is arranged coaxially with, and merges with, a cap support 36. The latter element of the assembly also is preferably cradled shaped. It is dimensioned to receive cap 28.

Means are provided for releasably securing cap 28 in cap holder 36. In the illustrated form of the invention, such means comprise a thumb screw 38 which, when advanced, bears against and retains cap 28 but which, when released or backed off, permits ready withdrawal of the cap from the holder.

Body support 34 has an open proximal end. It provides accommodation for finger grip 22 which, as illustrated, is of enlarged diameter.

A bracket 40 spaces a saddle-contoured support 42 for plunger 24 of the syringe.

It is to be noted that when the syringe is placed in the holder, as shown in FIG. 3, the proximal face of finger grip 22 is adjacent, and bears against, the inside face of plunger support 42. Its distal face is adjacent, and bears against, the end edge of syringe body support 34. This permits adjustment of the plunger position, onehanded, while a syringe is in the holder, should such adjustment be desired.

Clamp means are provided for releasably clamping the holder assembly to a structural element of dental cart 12, or other desired structure. As illustrated in FIG. 2, the clamp means comprises a U-shaped member 44 provided with thumb screw 46.

It is a feature of the present invention that the syringe holder may be associated with a holder for a scalpel or other related implement having a sharp edge which it is desired to sheath. As illustrated in FIGS. 2 and 6, the scalpel holder may comprise a simple sheath 48 having on its lower end a tongue 50. The latter element is dimensioned for insertion in a groove or slot 52 in a friction fit in the upper surface of clamp member 44. The sheath is designed to contain the cutting blade of a scalpel 54.

All of the elements of the herein described assembly are constructed of stainless steel or other suitable structural material capable of being autoclaved for sterilization.

The manner of use of the syringe holder of my invention is as follows:

At the beginning of each use, a fresh, sterile syringe holder is provided with a needle 18 sheathed in cap 30. The entire assembly is placed in the holder, with the body 16 of the syringe supported by body support 34, cap 30 containing needle 18 by cap support 36, and plunger 24 by bracket 40. Thumb screw 38 is tightened down on the cap to hold it in place.

When the doctor calls for the syringe, the implement may be removed from the holder easily by picking it up and withdrawing the needle from the sheath.

After use, the syringe may be replaced in the holder by reversing the operation. This sequence may be consummated as many times as desired, including the step of recharging barrel 16 with a fresh anesthetic or other cartridge if this is desired. At the same time, scalpel 54 may be inserted in scalpel holder 48 and used from time to time as desired.

After final use of the syringe, thumb screw 38 is released. Thereupon the syringe assembly including protective cap 30 may be removed from the holder and sent to disposal or to autoclaving, after removal of the needle. Similarly, scalpel holder 48 of the contained scalpel 54 may be removed from slot 52 and suitably processed. These operations may be effectuated using one hand. The possibility of a needlestick from handling the syringe, or of cutting from handling the scalpel, are entirely eliminated.

Having thus described in detail a preferred embodiment of the present invention, it will be apparent to those skilled in the art that various physical changes may be made in the invention described herein without altering the inventive concepts and principles embodied. The present embodiment is therefore to be considered as illustrative and not restructive, the scope of the invention being indicated by the appended claims rather than by the foregoing description. All changes which come within the meaning and range of equivalency of the claims are therefore to be embraced therein.

I claim:

1. For use together with a syringe assembly comprising a syringe body, a syringe needle attached to one end of the body, a finger grip attached to the other end of the body, an operating piston working within the body and extending outwardly through the finger grip, and a protective cap for the needle, open at one end; a syringe holder comprising:
    (a) a syringe body support comprising a cradle-shaped support member, open at the top
    (b) a cap support at one end of the body support arranged therewith the open end of the cap facing inwardly, the cap support comprising a cradle-shaped member, open at the top and merging with the body support; and
    (c) releasable cap securing means positioned for releasably securing the cap in a position to receive the syringe needle when the syring body is placed on the syringe body support, to secure the cap when the syringe is removed from the syringe body support after each use, and to release the cap when the syringe and cap are removed together from the support for disposal after use.

2. For use together with a syringe assembly comprising a syringe body, a syringe needle attached to one end of the body, a finger grip attached to the other end of the body, an operating piston working within the body and extending outwardly through the finger grip, and a protective cap for the needle, open at one end; a syringe holder comprising:
    (a) a syringe body support;
    (b) a cap support at one end of the body support arranged therewith with the open end of the cap facing inwardly;

(c) releasable cap securing means positioned for releasably securing the cap in a position to receive the syringe needle when the syringe body is placed on the syringe body support, to secure the cap when the syringe is removed form the syringe body support after each use, and to release the cap when the syringe and cap are removed together from the support for disposal after use;

(d) the syringe body support comprising a cradle-shaped member open at the top and open at the end opposite the cap support; and (e) bracket means spaced longitudinally from the open end of the body support for accommodating the finger grip and piston elements of the syringe.

3. For use together with a syringe assembly comprising a syringe body, a syringe needle attached to one end of the body, a finger grip attached to the other end of the body, an operating piston working within the body and extending outwardly through the finger grip, and a protective cap for the needle, open at one end; a syringe holder comprising:

(a) a syringe body support;

(b) a cap support at one end of the body support arranged therewith with the open end of the cap facing inwardly;

(c) releasable cap securing means positioned for releasably securing the cap in a position to receive the syringe needle when the syringe body is placed on the syringe body support, to secure the cap when the syringe is removed form the syringe body support after each use, and to release the cap when the syringe and cap are removed together from the support for disposal after use;

(d) a base mounting the syringe body support;

(e) a scalpel holder comprising a scalpel sheath; and (f) tongue and groove mounting means releasably mounting the scalpel holder on the base.

* * * * *